BLUEGRASS PLANT

Filed Jan. 5, 1971 2 Sheets-Sheet 1

United States Patent Office

Plant Pat. 3,223
Patented June 27, 1972

3,223
BLUEGRASS PLANT

Kevin Joseph McVeigh, Somerset, and Cyril Reed Funk, Jr., Milltown, N.J., assignors to Rutgers University, New Brunswick, N.J.

Filed Jan. 5, 1971, Ser. No. 104,182
Int. Cl. A01h *5/00*
U.S. Cl. Plt.—88 1 Claim

ABSTRACT OF THE DISCLOSURE

A Kentucky bluegrass plant which exhibits an attractive, fresh, moderately light green color, an upright panicle, and rather small florets and spikelets. The plant produces a dense, upright turf of a unique, soft, velvety texture which has excellent horizontal spreading ability, excellent resistance to stripe smut and moderately good resistance to leaf spot and crown rot.

The present invention relates to a new and distinct variety of Kentucky bluegrass plant, and more particularly to a bluegrass plant which exhibits a unique, soft, velvety texture, excellent resistance to the stripe smut disease and an attractive, fresh, bright, moderately light green color.

The new variety was discovered by us in a cultivated lawn in New Brunswick, N.J. An attractive, vigorous, aggressive, low-growing, bright green patch of grass was observed in an area where most other bluegrass plants were doing poorly. Plant material from this spot was taken to a greenhouse where we asexually reproduced additional plants of the variety by the method of vegetative propagation. After growth in the greenhouse, the vegetatively reproduced plants were transferred to field nurseries for increase and subsequent turf evaluation. Progeny tests were conducted and showed that the plant could also be reproduced asexually by means of disseminules. The plant was identified as "NJE P–57" bluegrass.

NJE P–57 bluegrass exhibits a unique combination of characteristics which distinguishes it from all other varieties of which we are aware. Of special moment is its attractive, fresh bright green color which is maintained throughout the growing season, a soft, velvety texture and excellent resistance to stripe smut disease caused by the fungus *Ustilago striiformis*. The new variety has moderate resistance to powdery mildew disease caused by the fungus *Erysiphe graminis*, to leaf rust disease caused by the fungus *Puccinia poae-nemoralis* and the leaf spot and crown rot disease caused by the fungus, *Helminthosporium vagans*. The variety is highly apomictic and produces a dense, aggressive, leafy, persistent turf tolerant of moderately close mowing.

A primary object of this invention is to provide a new and distinct bluegrass plant having the desirable characteristics referred to above and to be described in detail below.

Other objects and advantages of the invention will become more fully apparent from the following detailed description when taken in conjunction with the accompanying illustrations, in which.

Figure 1:
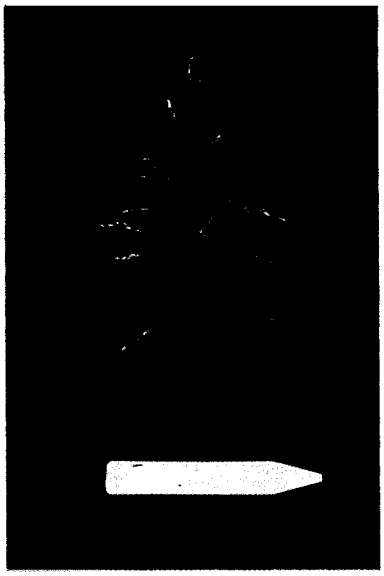
FIG. 1 shows a panicle of the new variety.
Figure 2:
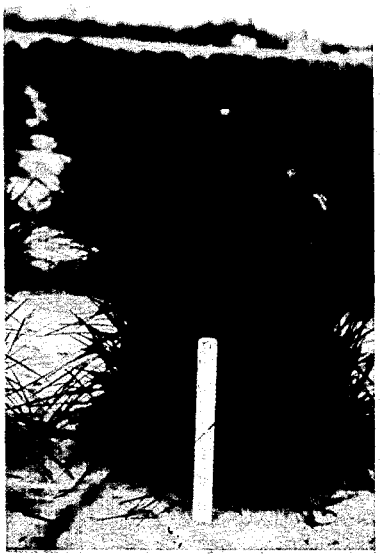
FIG. 2 shows a plant of the new variety approximately 10 days before the initiation of anthesis.
Figure 3:
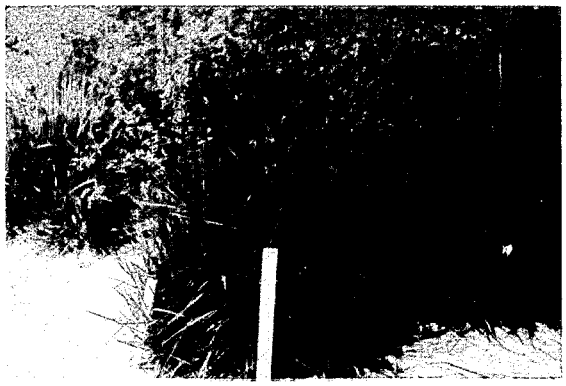
FIG. 3 shows a plant of the new variety under different lighting conditions after anthesis was completed.
Figure 4:
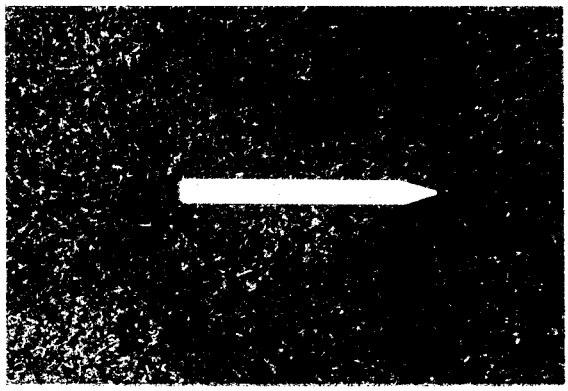
FIG. 4 shows a turf plot of the new variety.
Figure 5:
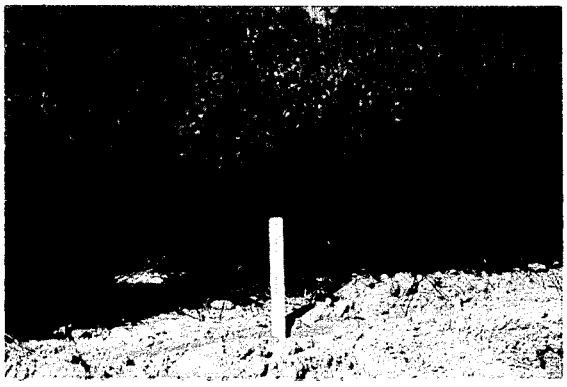
FIG. 5 shows a seed increase of the new variety.

NJE P–57 Kentucky bluegrass (*Poa pratensis* L.) is perennial with creeping rhizomes and forms a dense, upright, very aggressive turf. The variety exhibits the following unique combination of characteristics:

(1) Excellent resistance to the stripe smut disease incited by the fungus, *Ustilago striiformis*;

(2) Moderately good resistance to the leaf spot and crown rot disease caused by the fungus, *Helminthosporium vagans*;

(3) Moderate resistance to the leaf rust disease caused by the fungus, *Puccinia poae-nemoralis*;

(4) Moderate resistance to the powdery mildew disease caused by the fungus, *Erysiphe graminis*;

(5) A leafy turf-type growth habit tolerant of moderately close mowing;

(6) A very attractive, bright, fresh, moderately light green color;

(7) Very good rhizome and tiller development under turf maintenance producing a turf of excellent density and outstanding horizontal spreading ability;

(8) Leaves of medium width which produce a turf with a very unique soft, velvety texture;

(9) Rather small florets and spikelets;

(10) A very erect panicle;

(11) Very little purple on the edge of the lemmas;

(12) Later date of anthesis than most other Kentucky bluegrasses;

(13) Very good turf performance; and

(14) Excellent persistence in old turf trials at New Brunswick, N.J.

*Plant description*

The plants of the new variety which are described herein were grown at Adelphia, N.J. The culms of the variety are moderately bent at the lower nodes subsequently becoming rather erect. The culms are tufted and average 68 cm. in height when undisturbed by mowing, are moderately stout, cylindrical, usually with five nodes and smooth. Leaves are medium green; sheaths smooth with those on the vegetative shoots compressed and keeled; ligules membraneous with fine hairs, and very short on vegetative tillers but about 0.8 to 1.0 mm. long on reproductive tillers; edge of collar fringed with fine hairs; blades 2 to 4 mm. wide, initially folded but subsequently opening out with a boat-shaped apex; the flag leaf averages 60 mm. in length. Panicles pyramidal open, with main axis erect averaging 98 mm. long, the lowermost branches in whorls of usually 3 or 4 (average 3.7). Spikelets ovate, compressed, 3.6 to 5.0 mm. long, (average 5.0 mm.), 3 to 4 flowered (average 3.2) breaking up at maturity beneath each lemma. Glumes persistent, pointed, unequal, rough on the keels, lower ovate, 2.2 to 3.0 mm. long (average 2.6 mm.), 1 to 3 nerved; upper ovate to elliptic 2.7 to 3.4 mm. long (average 3.0 mm.), three-nerved. Lemmas five-nerved overlapping ovate-oblong in side view, slightly pointed, pubescent on the keel and the lower half of the marignal nerves, long fine crinkled hair at the base, thin tips and margins. Paleas about as long as lemmas with two rough keels. Caryopsis tightly enclosed by the hardened lemma and palea. Pollen production is sparse.

Since soil and climatic factors influence morphological characteristics to some degree these characters may vary slightly under different conditions. The morphological characteristics of NJE P–57 and other bluegrasses measured during 1970 at Adelphia, N.J., are shown in Table 1.

TABLE 1.—MORPHOLOGICAL COMPARISON OF NJE P-57 AND OTHER BLUEGRASS VARIETIES

| Variety | Plant | | Leaf blade width, mm. | Hairs on— | | Flag leaf length, mm. | Number of panicles plant | Panicle | | Number of branches at lowest panicle node | Panicle length mm. |
|---|---|---|---|---|---|---|---|---|---|---|---|
| | Height, cm. | Diameter, cm. | | Edge of collar [1] | Ligule [1] | | | Color [2] | Erect or nodding [3] | | |
| NJE P-57 | 68 | 38 | 3.6 | 1.5 | 1.0 | 60 | 279 | 1.0 | 1.5 | 3.7 | 98 |
| Delta | 73 | 17 | 2.6 | 1.5 | 0.0 | 67 | 196 | 2.0 | 1.0 | 4.8 | 100 |
| Geary | 80 | 24 | 2.9 | 2.0 | 0.0 | 80 | 177 | 3.0 | 3.0 | 4.0 | 134 |
| Newport | 79 | 30 | 4.8 | 3.7 | 3.7 | 77 | 246 | 2.5 | 2.0 | 4.3 | 105 |
| Palouse | 79 | 24 | 3.0 | 1.0 | 0.0 | 93 | 151 | 3.0 | 3.5 | 4.4 | 92 |
| Anheuser Dwarf | 67 | 30 | 5.1 | 2.5 | 2.0 | 51 | 109 | 3.0 | 2.5 | 3.4 | 96 |
| Belturf | 70 | 35 | 3.0 | 2.0 | 1.0 | 58 | 201 | 2.0 | 2.0 | 4.0 | 104 |
| Fylking (Patent 2,887) | 60 | 34 | 4.0 | 1.5 | 1.5 | 68 | 164 | 3.5 | 5.0 | 4.9 | 118 |
| Merion | 70 | 24 | 4.3 | 3.5 | 0.5 | 69 | 280 | 2.0 | 1.5 | 3.5 | 102 |
| Pennstar | 59 | 34 | 3.7 | 2.2 | 1.0 | 66 | 132 | 3.5 | 4.0 | 4.5 | 106 |

[1] Scale: 0=no hairs; 5=most hairs.
[2] Scale: 0=green; 5=purple.
[3] Scale: 1=erect; 5=nodding.

*Turf characteristics*

The new variety has exhibited consistently high turf performance ratings. The turf is attractive, leafy, soft and dense.

Overall turf performance ratings for NJE P–57 and other bluegrass varieties at New Brunswick, N.J., are presented in Table 2.

TABLE 2.—TURF PERFORMANCE RATINGS OF NJE P-57 AND OTHER BLUEGRASSES

| Variety | Turf performance (9=best) | | |
|---|---|---|---|
| | Test 1, 1964 to 1969 | Test 2, 1965 to 1970 | Test 3, 1967 to 1970 |
| NJE P-57 | 7.2a [1] | 7.6a | 7.1a |
| Fylking | 7.6a | 7.3a | 7.1a |
| Merion | 5.4b | 5.6b | 6.2b |
| Windsor (Patent 2,364) | 3.0c | 5.2bc | 5.1c |
| Delta | 2.4c | 4.7c | 3.5d |

[1] Values within a column followed by the same letter do not differ significantly at the five percent probability level.

*Disease resistance*

A comparison of NJE P–57 and other bluegrasses for resistance to stripe smut caused by the fungus *Ustilago striiformis*, leaf spot and crown rot caused by the fungus *Helminthosporium vagans*, leaf rust caused by the fungus *Puccinia poae-nemoralis*, and powdery mildew caused by the fungus *Erysiphe graminis* is presented in the following tables:

TABLE 3.—RELATIVE COMPARISON OF STRIPE SMUT DISEASE RESISTANCE OF NJE P-57 AND OTHER BLUEGRASSES AT NEW BRUNSWICK, N.J.

| Variety | Test 1, 1964 to 1969—Stripe smut reaction [1] | Test 2, 1965 to 1970—Stripe smut infected tillers per square foot |
|---|---|---|
| NJE P-57 | 1a [2] | 0a |
| Fylking | 2b | 0a |
| Delta | 3c | 9b |
| Windsor | 6d | 41c |
| Merion | 8e | 228d |

[1] Scale: 1=most resistant; 8=least resistant.
[2] Values within a column followed by the same letter do not differ significantly at the five percent probability level.

TABLE 4.—RELATIVE COMPARISON OF LEAF SPOT AND CROWN ROT DISEASE RESISTANCE FOR NJE P-57 AND OTHER BLUEGRASSES AT NEW BRUNSWICK, N.J.

| Variety | Percent leaf spot damage | | |
|---|---|---|---|
| | Test 1, 1964 to 1969 | Test 2, 1965 to 1970 | Test 3, 1967 to 1970 |
| Merion | 11a[1] | 5a | 5a |
| Fylking | 15a | 6a | 6a |
| NJE P-57 | 13a | 18b | 12b |
| Windsor | 35b | 28c | 25c |
| Delta | 48c | 70d | 80d |
| Park | | | 85de |
| Kenblue | | | 90e |
| South Dakota Common | | | 95ef |
| Troy | | | 98f |

[1] Values followed by the same letter do not differ significantly at the five percent probability level.

TABLE 5

Relative comparison of leaf rust disease resistance for NJE P–57 and other bluegrasses in New Jersey

| Variety: | Rust disease rating [1] |
|---|---|
| Fylking | 1.5 a [2] |
| Delta | 1.5 a |
| NJE P–57 | 2.5 b |
| Merion | 3.5 c |
| Newport | 3.5 c |
| NJE P–117 | 7.5 d |

[1] Scale: 0=no rust; 9=most disease.
[2] Values followed by the same letter do not differ significantly at the five percent probability level.

TABLE 6

Relative comparison of powdery mildew disease resistance of NJE P–57 and other bluegrasses under greenhouse conditions at New Brunswick, N.J.

| Variety: | Mildew rating [1] |
|---|---|
| Newport | 0.8 a |
| Windsor | 2.5 b |
| NJE P–57 | 3.9 c |
| Fylking | 3.9 c |
| Merion | 6.9 d |

[1] Values followed by the same letter do not differ significantly at the five percent probability level.

The tests summarized in the foregoing tables show that NJE P–57 has excellent resistance to stripe smut, moderately good resistance to leaf spot and moderate resistance to powdery mildew and leaf rust.

*Aggressiveness*

The new variety is very aggressive under turf maintenance as shown in the following tables:

TABLE 7

Aggressiveness of various bluegrass varieties as measured by their ability to spread under conditions of close mowing and competition from other bluegrasses

| Variety: | Amount of incroachment into adjacent bluegrass varieties "inches" |
|---|---|
| NJE P–57 | +14.0a [1] |
| Pennstar | +2.5b |
| Fylking | +2.5b |
| Anheuser Dwarf | +2.0b |
| Merion | −1.5c |
| Windsor | −1.5c |
| Delta | −3.0c |

[1] Values followed by the same letter do not differ significantly at the five percent probability level.

TABLE 8

Aggressiveness of various bluegrass varieties as measured by their ability to speed under conditions of close mowing and competition from other turfgrasses

| Variety: | Amount of spread per plant [1], square inches |
|---|---|
| NJE P–57 | 2290a [2] |
| Anheuser Dwarf | 415b |
| Merion | 269c |

[1] Individual tillers of each variety were established in a clonal nursery which was interseeded with perennial ryegrass and maintained for 6 years under close mowing.
[2] Numbers followed by the same letter do not differ significantly at the five percent probability level.

*Time of anthesis*

The new variety is later flowering than most other Kentucky bluegrass varieties as shown in Table 9.

TABLE 9

Date of initiation of anthesis of Kentucky bluegrass variety at Aldelphia, N.J.

| Variety: | Date first flowers open |
|---|---|
| Delta | May 20a [1] |
| Nugget | May 23b |
| Newport | May 25c |
| Fylking | May 26cd |
| Anheuser Dwarf | May 27d |
| Merion | May 29e |
| NJE P–57 | June 2f |

[1] Dates followed by the same letter do not differ at the five percent probability level.

*Reproduction and propagation*

Asexual reproduction of NJE P–57 by propagules (tillers and rhizomes) and by disseminules (modified caryopses produced by agamospermy) has consistently produced progeny plants indistinguishable from the mother plant.

What is claimed is:

1. A new and distinct variety of Kentucky bluegrass plant, substantially as herein shown and described, characterized by very good turf performance, an excellent record of persistence under adverse conditions, an aggressively spreading upright turf having a unique, soft, velvety texture with an attractive, bright, fresh, moderately light green color and excellent resistance to stripe smut disease.

No references cited.

ROBERT E. BAGWILL, Primary Examiner